(12) United States Patent
Fayolle

(10) Patent No.: US 10,025,965 B2
(45) Date of Patent: Jul. 17, 2018

(54) METHOD, DEVICE AND INSPECTION LINE FOR THE OPTICAL READING OF RELIEFS ON A SIDE WALL OF A CONTAINER

(71) Applicant: TIAMA, Vourles (FR)

(72) Inventor: Lubin Fayolle, Brignais (FR)

(73) Assignee: TIAMA, Vourles (FR)

( * ) Notice: Subject to any disclaimer, the term of this patent is extended or adjusted under 35 U.S.C. 154(b) by 0 days.

(21) Appl. No.: 15/518,524

(22) PCT Filed: Oct. 9, 2015

(86) PCT No.: PCT/FR2015/052718
§ 371 (c)(1),
(2) Date: Apr. 12, 2017

(87) PCT Pub. No.: WO2016/059326
PCT Pub. Date: Apr. 21, 2016

(65) Prior Publication Data
US 2017/0235985 A1    Aug. 17, 2017

(30) Foreign Application Priority Data

Oct. 17, 2014 (FR) .................................... 14 60030

(51) Int. Cl.
*G06K 7/14* (2006.01)
*G06K 7/10* (2006.01)

(52) U.S. Cl.
CPC ..... *G06K 7/10861* (2013.01); *G06K 7/10722* (2013.01); *G06K 7/10831* (2013.01)

(58) Field of Classification Search
CPC ... G06K 7/10722; G06K 7/14; G06K 7/10851
(Continued)

(56) References Cited

U.S. PATENT DOCUMENTS 6,072,575 A * 6/2000 Loll .................... G01N 21/9054
356/239.1
6,621,573 B2 * 9/2003 Shultz ................ G01N 21/9045
356/239.4
(Continued)

FOREIGN PATENT DOCUMENTS

DE     299 20 232    12/2000
EP     1 010 126     6/2000
(Continued)

*Primary Examiner* — Ahshik Kim
(74) *Attorney, Agent, or Firm* — Clark & Brody

(57) ABSTRACT

A method, device, and inspection line for optically reading portions in relief on a side wall of a container, includes using a light source to light a portion of interest with a peripheral incident light beam comprising non-parallel radial light rays and using specular reflection of the beam on the portion of interest and on the portions in relief through an optical element to form a plane image in the field of view of a two-dimensional photoelectric sensor. The image received by the sensor is processed in order to detect the portions in relief to cause the light source that provides the peripheral incident light beam to move relative to the optical element in translation along the direction of a theoretical central axis to modify the contrast of the image received by the sensor between zones of the image that correspond to the portions in relief and adjacent zones.

27 Claims, 7 Drawing Sheets

(58) Field of Classification Search
USPC .......................................................... 235/454
See application file for complete search history.

(56) References Cited

U.S. PATENT DOCUMENTS

| | | | |
|---|---|---|---|
| 7,057,718 B2* | 6/2006 | Kwirandt | G01N 21/9027 250/223 B |
| 9,316,600 B2* | 4/2016 | Kurosawa | B07C 5/3408 |
| 2012/0176655 A1* | 7/2012 | Shirakura | G03H 1/2205 359/32 |
| 2015/0227804 A1* | 8/2015 | Kobayashi | G06K 9/209 382/142 |

FOREIGN PATENT DOCUMENTS

| | | |
|---|---|---|
| EP | 1 494 010 | 1/2005 |
| EP | 1 952 898 | 8/2008 |
| FR | 2 986 326 | 8/2013 |
| WO | 00/00924 | 1/2000 |

* cited by examiner

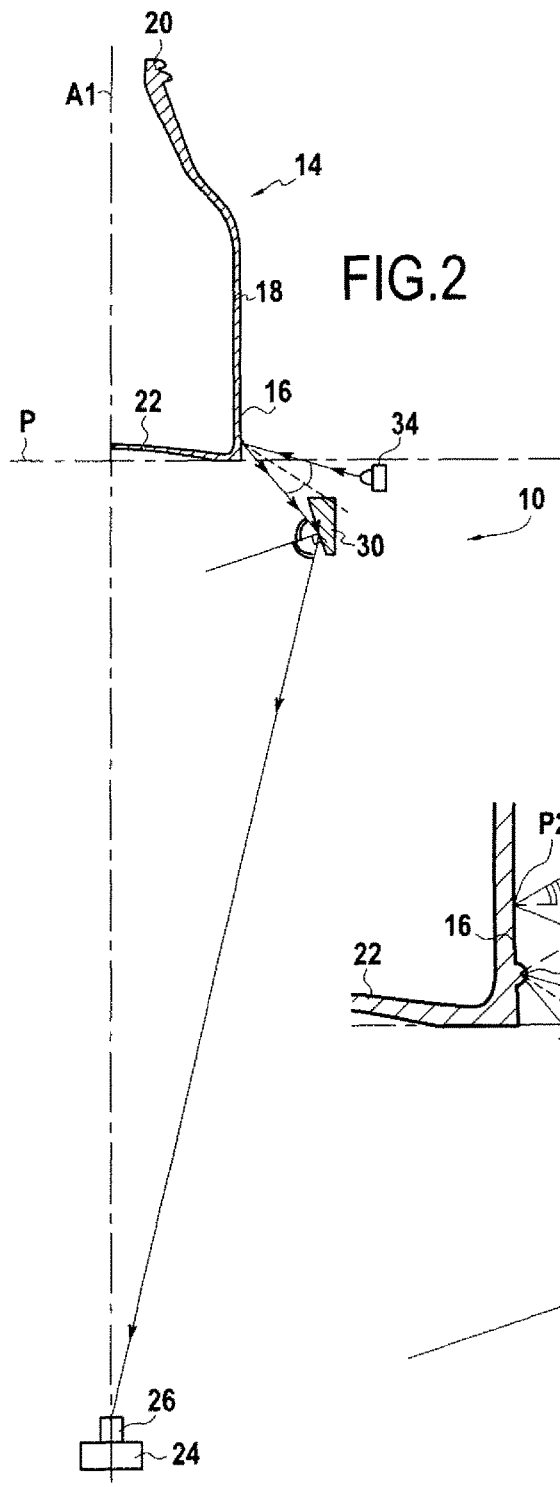

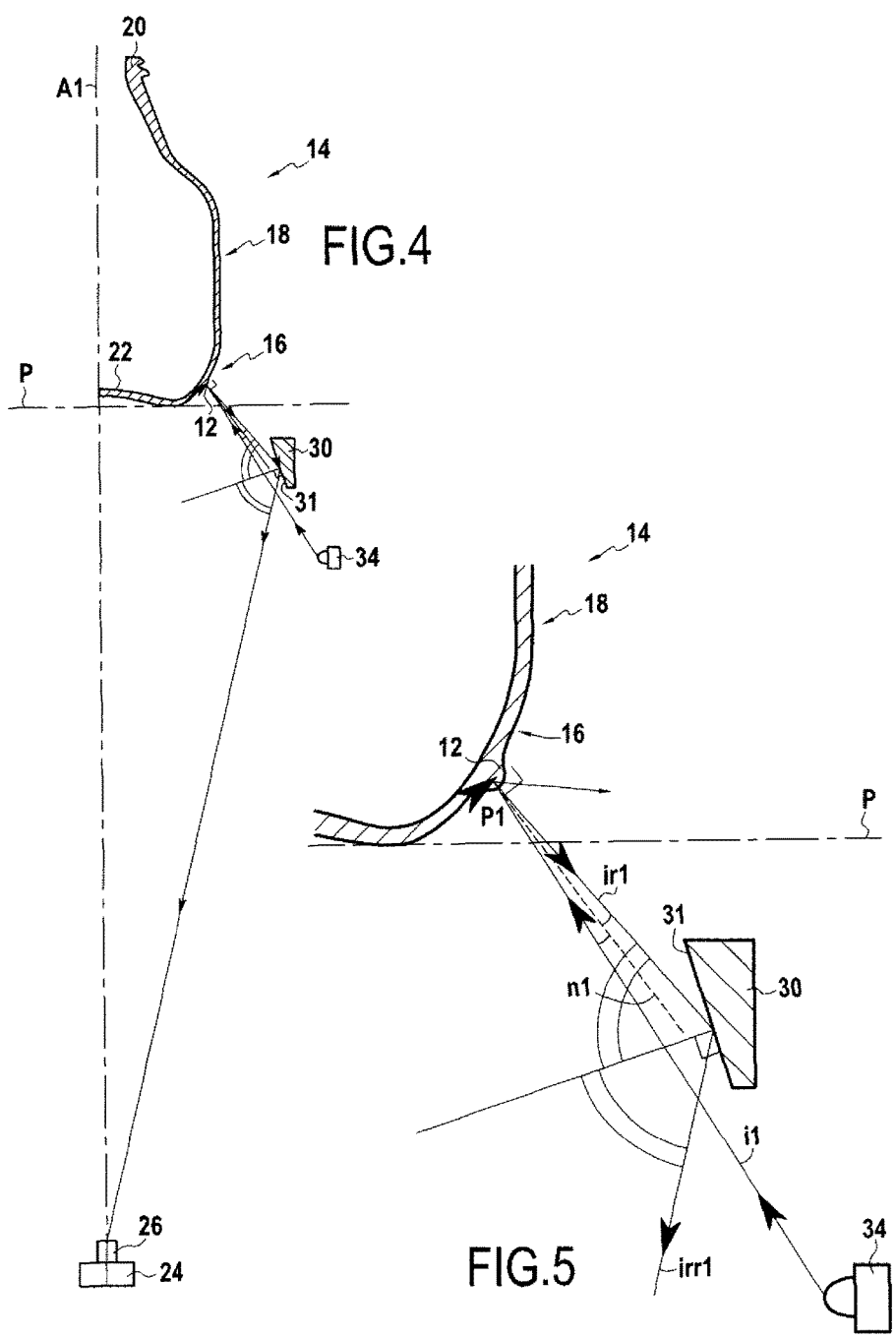

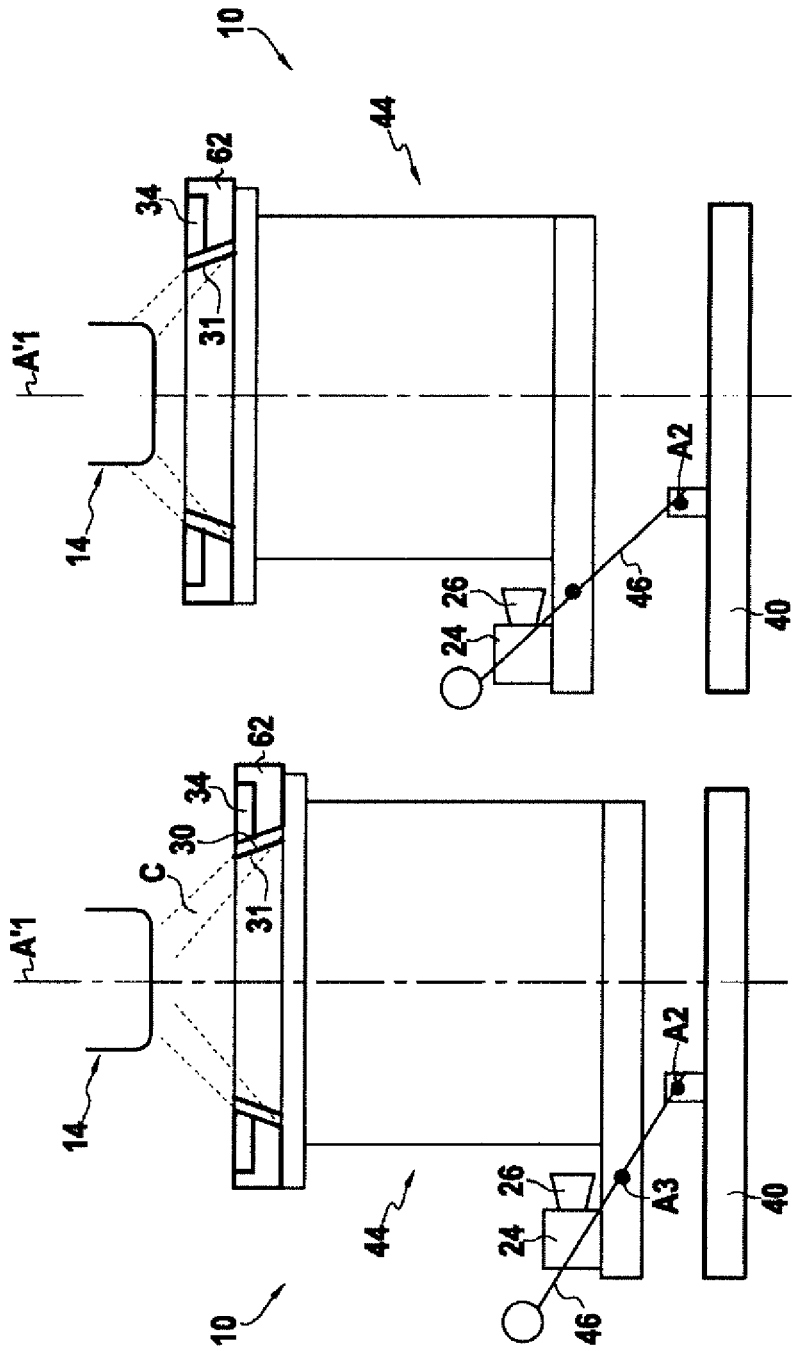

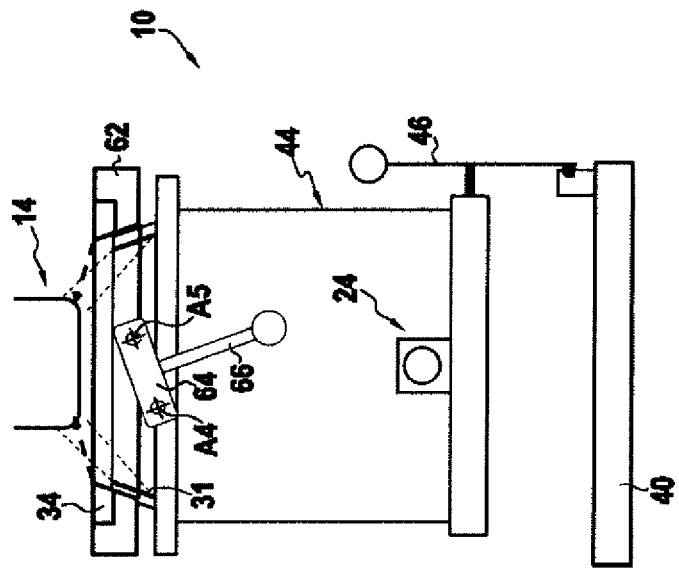
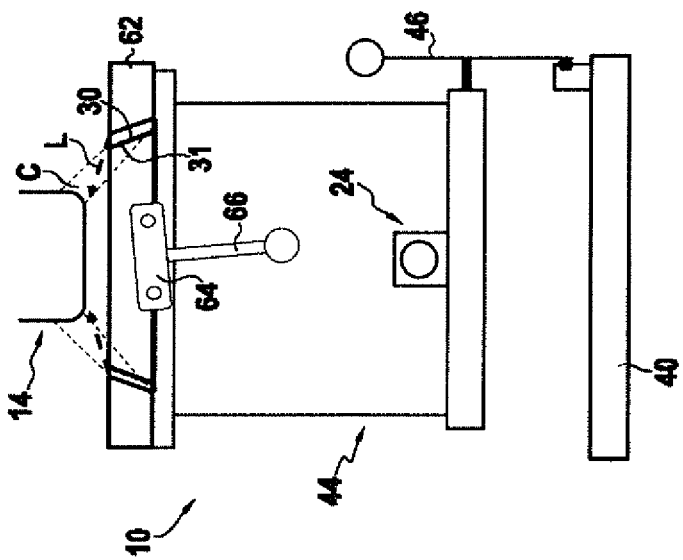

METHOD, DEVICE AND INSPECTION LINE FOR THE OPTICAL READING OF RELIEFS ON A SIDE WALL OF A CONTAINER

FIELD OF THE INVENTION

The invention relates to a method and a device for optically reading portions in relief forming an identification code on a container.

BACKGROUND ART

One of the applications of the invention seeks to read a mold number written a portion of the outer side wall of a container, e.g. on the insweep of a bottle, in particular a glass bottle. In certain circumstances, this number is written in the form of a code made up of portions in relief, e.g. beads, formed on the insweep (or "heel"), i.e. the bottom end of the side wall of the container. In this context, it is important to identify the positions of these portions in relief, in particular their angular positions, in order to be able to deduce therefrom the code and thus the mold number.

In the preferred field of application of the invention, it is known to read a mold number carried by containers, e.g. in order to associate potential defects as may be detected by dedicated sensors with the number of the defective mold. It is thus possible for containers fabricated by a defective mold to be rejected automatically. Reading an identification code can also make it possible to take containers coming from one or more molds automatically, in particular for sampling purposes. The subject matter of the invention thus also finds another advantageous application in the field of sorting empty or full containers by mold number. Various devices have already been proposed in the prior art. Some of those devices require the container to be pivoted about its central axis in front of a reader device, and they are thus complicated, and they also slow down conveyor operations.

Document EP 1 010 126 describes a method of optically reading portions in relief forming an identification code. In the method described in that document, provision is made to light the portion of interest of the outer side wall of the container, which portion is limited along the direction of an installation axis but extends over 360° around the installation axis. In an example, the insweep of a glass bottle is lit in that way. The lighting is performed using a light source that provides a peripheral incident light beam having radial light rays contained in a radial plane containing the installation axis. The radial rays are directed towards the installation axis and the beam as generated in this way comprises non-parallel radial rays in a common radial plane. The method described in that document makes provision for using an optical element, specifically a concave frustoconical mirror flaring downwards away from an installation zone in which the container for observation is placed, to form a plane image of the portion of interest of the wall of the container. An optical system is used to form this image in the field of view of a matrix photoelectric sensor. The method then includes the step of processing the image received by the sensor in order to detect the portions in relief in order to be able to decode the identification code.

In order to perform that method, Document EP 1 010 126 describes a device that is contained entirely below the installation zone of the container and that includes a lighting system, e.g. using an annular optical fiber, for delivering an incident light cone serving to light the entire periphery of the insweep of the container. The device also has a matrix camera, i.e. a camera capable of recovering two-dimensional images, for the purpose of receiving the image of the portion of interest of the outside surface of the container. An optical system is interposed between the installation zone and the sensor in order to form an image on the sensor of the portion of interest of the outer side wall of the container. The optical system has an optical element constituted by a circularly symmetrical frustoconical optical mirror. The optical system also has a standard objective lens incorporated in the matrix camera and a deflection mirror arranged at 45° relative to an installation axis corresponding both to the central axis of the incident light source and to the central axis of the optical element. The camera can thus be placed at 90° relative to the installation axis in order to reduce the overall size of the device along the direction of that axis. The optical system, taken overall between the sensor and the installation zone for receiving a container for observation can thus be said to present an optical axis made up of two mutually-orthogonal main portions: one beside the camera, and the other beside the installation zone. The advantage of the device described in that document lies in the fact that the lighting system, the sensor, and the optical system are arranged below the installation zone that is to receive a container for observation, the installation zone being the observation zone of the device. As a result, it is possible to move the container perpendicularly to its central axis in order to bring it into the installation zone. Such a device is thus easily installed below a line for conveying bottles or containers without interfering with the movement of the containers, it being understood that as a general rule container conveyor systems move containers along a travel path that is perpendicular to the axis of their central axes.

The device described in Document EP 1 010 126 is thus particularly suitable for reading portions in relief carried on the side wall of a container without requiring any element of the device to be at the same height as the portion of interest on the side wall where it is desired to read such portions in relief. Furthermore, by means of its lighting and peripheral vision system, making it possible to observe 360° around the axis of the container, that device and that method do not require the container or the reader device to be set into rotation.

It can be understood that the device and the method described in Document EP 1 010 126 make use of the fact that the incident light beam is reflected at least in part by specular reflection on the portion of interest of the outer side wall of the container and on its portions in relief.

That device is entirely satisfactory in most application situations. Nevertheless, under certain circumstances, it has been found that that device and that method need to be modified in order to read portions in relief under certain conditions. Specifically, depending on the shape of the outer side wall and as a function of the shape of the portions in relief carried on that surface, circumstances can exist in which the optical system of the sensor can no longer distinguish light rays reflected by the portions in relief from rays reflected by the remainder of the insweep. With that device, it is possible to adjust the angle observation each time there is a change of article being fabricated, but to do that it is necessary to change the optical element and thus to have a wide range of conical observation mirrors presenting different geometrical characteristics. Unfortunately, such mirrors are expensive, and changing mirrors is a manual operation that pointlessly lengthens the time needed for adjustment, which is not satisfactory from an operational point of view. Furthermore, such adjustment by changing mirrors does not enable the operator to observe in real time the effects of the change by monitoring the result of the change as produced in the image. In certain circumstances, the operator wastes time selecting the best conical mirror from a range. Finally, adjustment by means of a range of parts allows for a limited number only of configurations.

SUMMARY OF THE INVENTION

The invention thus seeks to propose a novel method and a novel device that can easily be adapted to different shapes of container and portions in relief in order to read portions in relief with a good level of performance.

To this end, the invention provides a method of optically reading portions in relief forming an identification code, the portions in relief being carried by an outer side wall of a container having a theoretical central axis, the method being of the type comprising the steps consisting in:

using a light source to light a portion of interest of the outer side wall of the container, which portion is limited in the direction of an installation axis, but extends over 360° around the theoretical central axis, the light source supplying a peripheral incident light beam comprising radial light rays contained in a radial plane containing the theoretical central axis, and the beam including non-parallel radial rays in a common radial plane;

using at least one optical element to form a plane image of the portion of interest of the wall of the container in the field of view of a two-dimensional photoelectric sensor;

processing the image received by the sensor in order to detect the portions in relief;

the method being of the type in which the incident light beam is reflected at least in part by specular reflection on the portion of interest of the outer side wall and on the portions in relief;

the method being characterized in that it further includes the step consisting in causing the light source supplying the peripheral incident light beam to move in translation along the direction of the theoretical central axis relative to the optical element in order to modify the contrast in the image received by the sensor between zones of the image corresponding to the portions in relief and adjacent zones of the image corresponding to zones of the portion of interest of the wall of the container that are adjacent to the portions in relief.

According to optional other characteristics of such a method:

it includes a step of optimizing the movement of the source, consisting in searching for at least one position of the source along the direction of the theoretical central axis relative to the optical element in which contrast between the zones of the image corresponding to the portions in relief and adjacent zones of the image corresponding to zones of the portion of interest of the wall of the container that are adjacent to the portions in relief is at a level that is greater than a predetermined level.

it includes a step of moving the optical element along the direction of the installation axis in order to bring the portion of interest of the wall of the container into the field of view of the sensor, and in that the step consisting in causing the main light source to move relative to the optical element is performed after the step of moving the optical element.

in a radial plane containing the theoretical central axis, the light source is seen from a point of the portion of interest of the side wall of the container at a viewing angle of less than 15 degrees, preferably less than 5 degrees.

the step of optimizing the movement of the source is automated.

The invention also provides a device for optically reading portions in relief carried by a portion of interest of an outer side wall of a container, the device being of the type in which it presents a container installation zone having an installation axis, and of the type comprising:

a two-dimensional photoelectric sensor;

an optical system interposed between the container installation zone and the sensor in order to form on the sensor an image of the portion of interest of the outer side wall of a container placed in the installation zone, the optical system including at least one optical element having a reflection surface of revolution around the installation axis and presenting a minimum diameter greater than a maximum diameter of the portion of interest of the outer side wall of a container susceptible of being received in the installation zone;

an optical axis defined by the optical system and extending in the installation zone in order to define the installation axis; and a lighting system including at least a main light source that is peripheral and has the installation axis as its axis, and that is suitable for supplying a peripheral incident light beam in the installation zone, the beam comprising radial rays contained in a radial plane containing the installation axis, said radial rays being directed towards the installation axis, and the beam comprising non-parallel radial rays in a common radial plane;

and of the type in which the lighting system, the sensor, and the optical system are arranged below the installation zone;

the device being characterized in that the main light source supplying the peripheral incident light beam is movable in translation along the direction of the installation axis relative to the optical element.

According to optional other characteristics of such a device:

the main light source is movable between a multitude of distinct blocked positions along the direction of the installation axis, the blocked positions extending between two extreme positions.

the main light source is movable between a multitude of predefined discrete blocked positions relative to the optical element.

it includes at least two positions for the main light source relative to the optical element, and preferably at least three blocked positions.

the main light source can be blocked in any position relative to the optical element between two extreme positions.

it includes control means for controlling the movement of the main light source in translation along the direction of the installation axis relative to the optical element.

it includes blocking means for blocking the main light source in its blocked positions relative to the optical element.

the optical element is movable relative to the photoelectric sensor along the direction of the installation axis for bringing the portion of interest of the wall of the container into the field of view of the photoelectric sensor through the optical system.

it includes movement means for moving the optical element relative to a base of the device, and in that the movement means for moving the main light source relative to the optical element operate independently of the movement means for moving the optical element relative to the base.

the movement means for moving the optical element cause the main light source to move simultaneously with the optical element relative to the base.

the optical element is secured to a primary carriage that is movable relative to the base along the direction of the installation axis, in that the main light source is secured to a secondary carriage that is movable relative to the primary carriage along the direction of the installation axis, and in that a movement of the primary carriage gives rise to an equal movement of the secondary carriage.

the main light source is movable between at least two extreme positions along the direction of the installation axis, which extreme positions are on respective opposite sides of the axial position of the reflection surface of the optical element.

the lighting system includes an auxiliary light source that is annular, having the installation axis as its axis, and that is suitable for supplying an annular peripheral incident light beam distinct from the main beam supplied by the main light source, the auxiliary beam comprising radial rays contained in a radial plane containing the axis, said radial rays being directed towards the installation axis, and the auxiliary beam comprising, in a common radial plane, non-parallel radial rays, in that the main and auxiliary light sources are offset along the direction of the installation axis, and in that the auxiliary source is in a position that is stationary relative to the optical element.

the main light source is movable between at least two extreme positions along the direction of the installation axis, both of which are on the same side of the axial position of the reflection surface, and in that the auxiliary light source is arranged on the other side of the axial position of the reflection surface.

the reflection surface is a surface of revolution about the installation axis and faces towards the installation axis, and in that the reflection surface flares along the direction of the installation axis and presents a large diameter and a small diameter, both of which are greater than the maximum diameter of the portion of interest of the side wall of the container, the large diameter being arranged below the small diameter.

the reflection surface is a frustoconical surface facing towards the installation axis.

the sensor is arranged below the reflection surface.

the optical system includes an optical objective system associated with the sensor.

the container is to be received in the installation zone in such a manner that its theoretical central axis substantially coincides with the installation axis.

the device includes a base, and in that the photoelectric sensor and the optical element are fastened relative to each other and movable relative to the base.

The invention also provides an inspection line for inspecting containers each presenting portions in relief carried by a bottom portion of an outer side wall, the line being of the type in which the containers are moved along a conveyor line by a conveyor that transports the containers in a horizontal travel direction perpendicular to a theoretical central axis of each container, such that the containers present the bottom portions of their outer side walls facing downwards, the line being characterized in that the line includes a device having according to any of the preceding characteristics, which is arranged on the line with its installation axis in a vertical position, in such a manner that the incident light beam is upwardly oriented towards the installation zone that is situated between the device and a transport member of the conveyor.

In such an inspection line, the conveyor brings the containers in such a manner that their theoretical central axes coincide with the installation axis, and when they are in coincidence, an image is acquired using the device, without the device making contact with the container.

BRIEF DESCRIPTION OF THE DRAWINGS

Various other characteristics appear from the description made below with reference to the accompanying drawings, which show embodiments of the invention as non-limiting examples.

FIG. 2 is a view similar to FIG. 1 and shows more particularly the path of a light ray emitted by the lighting system and reflected in succession on a portion in relief of the bottle and by the optical system towards the sensor.

FIG. 3 is a diagram showing further details of the paths of various light rays in the FIG. 2 device.

FIG. 4 is a view similar to the view of FIG. 2, showing the lighting system in a second position, adapted to reading portions in relief on the insweep of a bottle of a different shape.

FIG. 5 is a view similar to the view of FIG. 3, showing the situation of FIG. 4.

FIGS. 9 and 10 are diagrammatic front views showing two positions of the optical element of the device.

FIGS. 11 and 12 are diagrammatic side views showing two positions of the light source relative to the optical element.

DETAILED DESCRIPTION OF THE INVENTION

Figure 1:
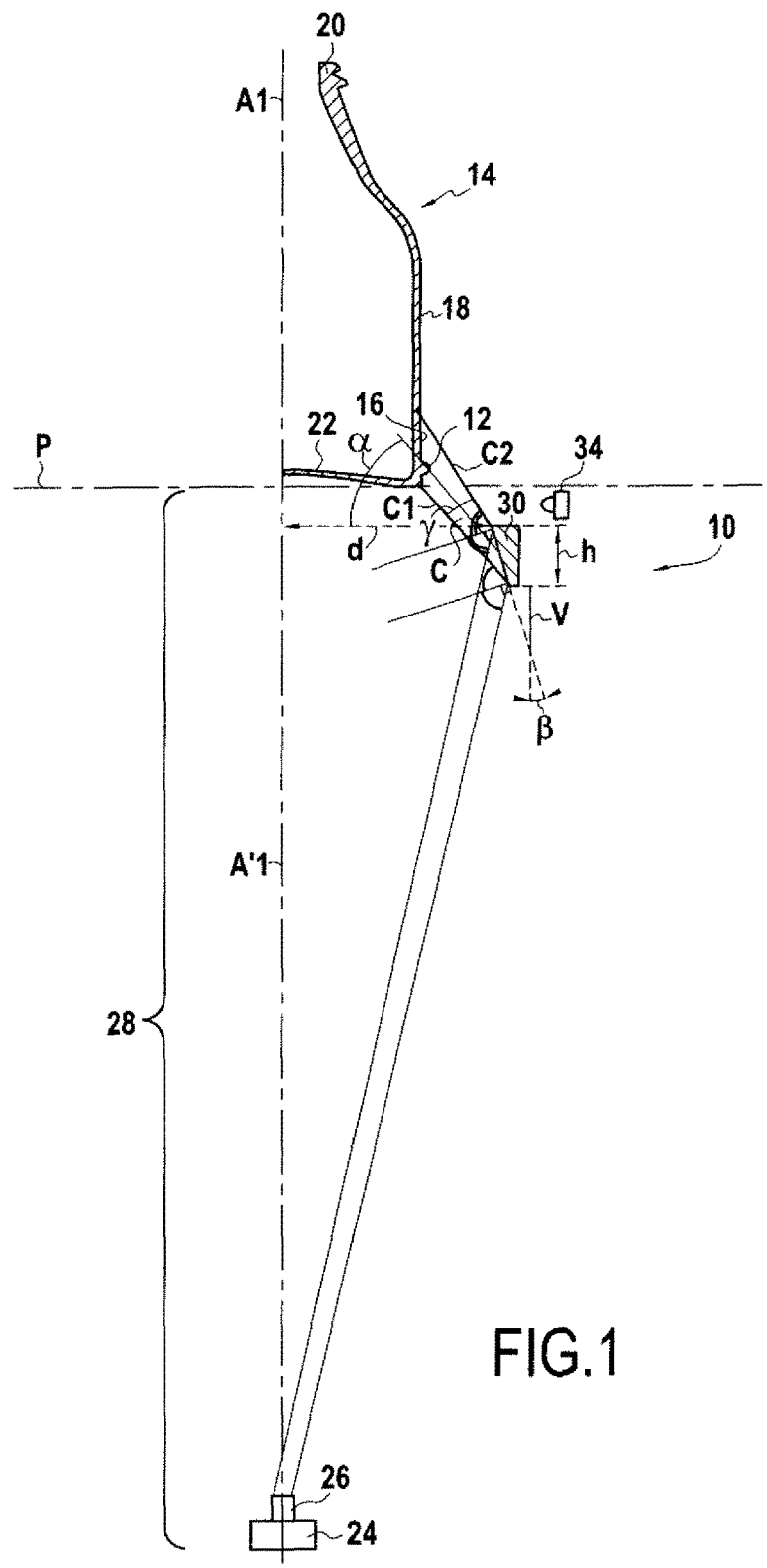
FIG. 1 is a theoretical diagram of an embodiment of a device and an implementation of a method of the invention. This figure shows the field of view of the sensor through the optical system of the invention making it possible to view the portion of interest of the side wall of the container.

FIGS. 1, 2, and 4 are diagrams showing the principle of an embodiment of a device 10 for optically reading portions in relief 12 carried by a portion of interest 16 of an outer side wall 18 of a container 14, the device of the invention enabling the method of the invention to be performed.

Figure 7:
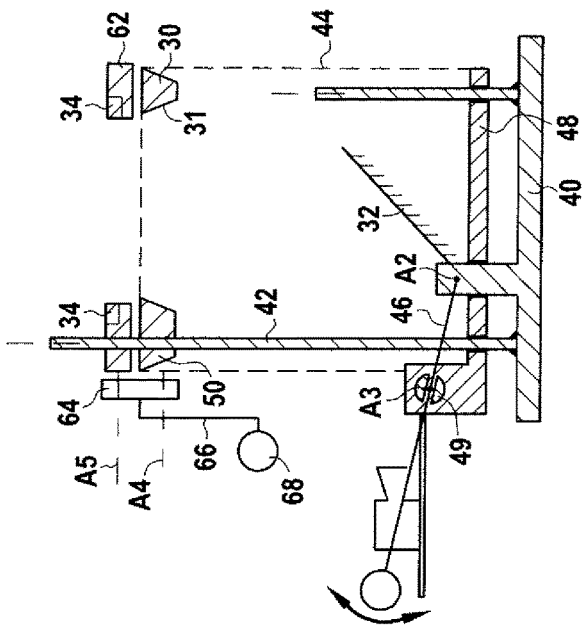
FIG. 7 is a diagrammatic side view of the FIG. 6 device showing in particular the means for moving the optical element relative to the installation zone and the means for moving the light source relative to the optical element.
Figure 6:
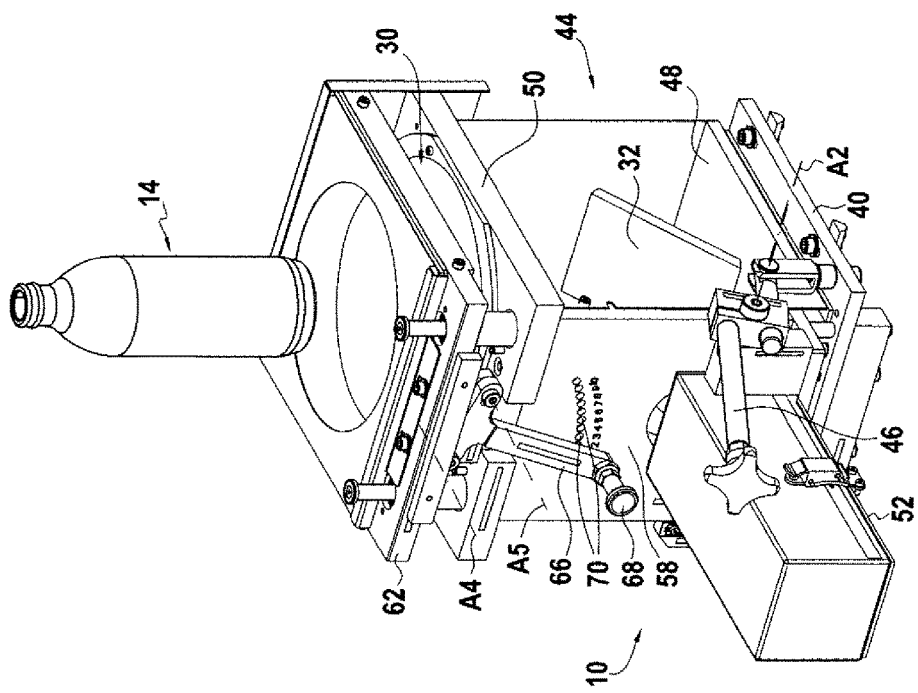
FIG. 6 is a perspective view showing an embodiment of a device of the invention.
Figure 8:
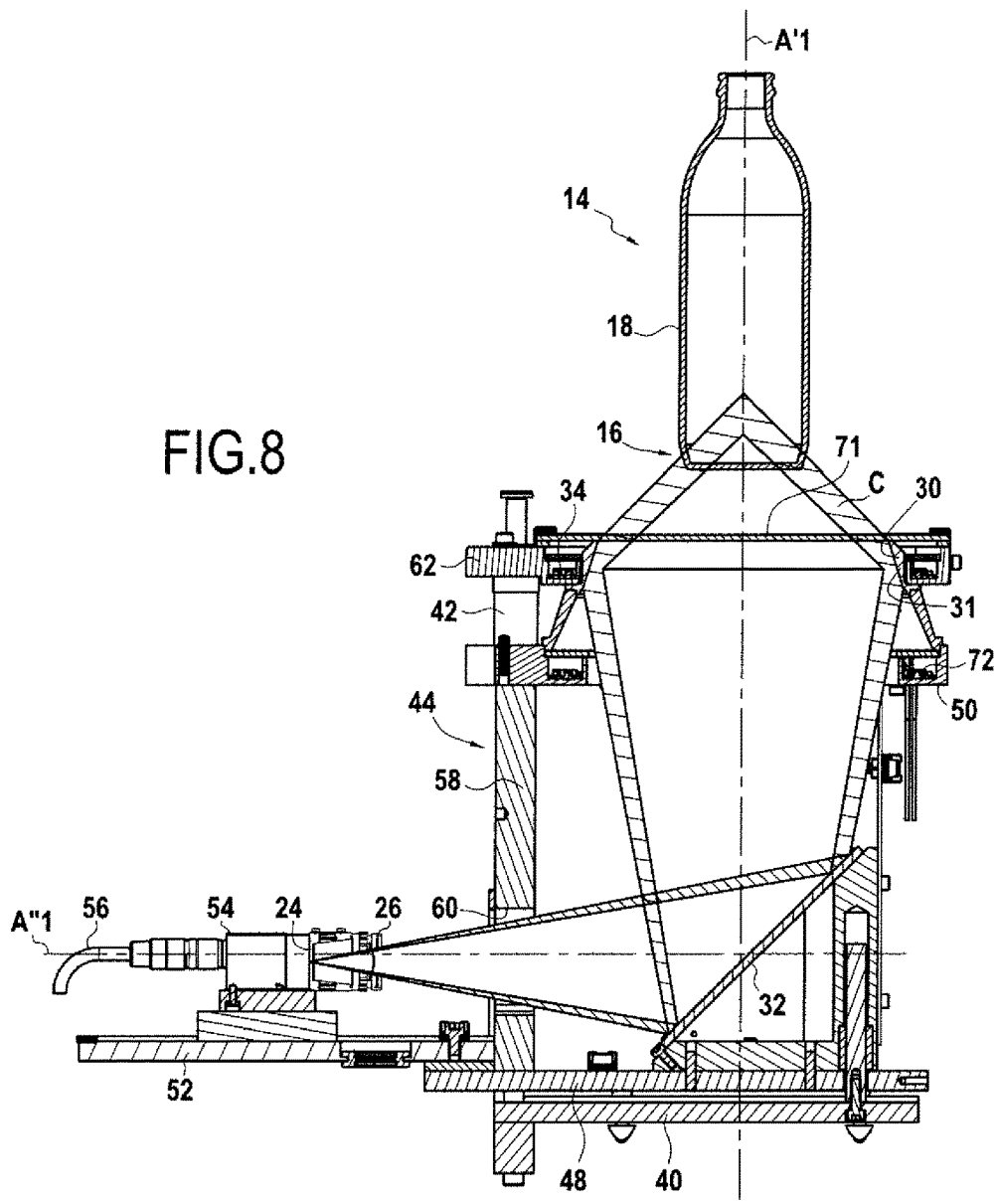
FIG. 8 is a side view in section showing the FIG. 6 system and showing more particularly the field of view of the sensor through the optical system of the invention.

FIGS. 6 to 8 show in greater detail an embodiment of a device of the invention suitable for performing a method of the invention. This embodiment makes use of the theoretical diagram of FIGS. 1, 2, and 4, with the sole modification that the optical system includes a deflector mirror between the optical element and the sensor, thereby segmenting the optical axis of the optical system into two mutually-orthogonal segments, enabling the sensor to be arranged on one side of the installation axis. Apart from this difference, the description below applies equally to the theoretical diagram and to the embodiment shown.

A container 14 is defined as a hollow container containing an inside volume that is closed over the entire periphery of the volume except at a top ring 20 that is open at one end.

For convenience, and purely by way of arbitrary definition, it is assumed that the container has a theoretical central axis A1 defined as being the theoretical central axis of the portion of interest 16 of the side wall 18. This theoretical axis A1 is generally an axis of symmetry of the container 14. It is also considered, arbitrarily, that the ring is arranged at the top end of the container. Thus, in the present description, the concepts of high, low, top, and bottom have relative values corresponding to the orientation of the device 10 and of the container 14 as shown in the figures. Nevertheless, it should be understood that the invention can be performed in any absolute orientation in three-dimensional space, insofar as the various components remain arranged in the same relative arrangement.

The ring 20 of the container is a circular cylinder about the theoretical central axis A1. The body of the container is defined by the side wall 18 and by a bottom wall 22 at its bottom end, which bottom wall is connected via its outer radial edge to the side wall 18 via a zone of the side wall 18 commonly referred to the insweep (or heel) 16, and in this embodiment it is the insweep that constitutes the portion of interest of the side wall 18. The body of the container 14 may optionally be a body of revolution. In the example described, the side wall 18 and the portion of interest 16 are bodies of revolution about the axis A1, and the bottom wall 22 is of a shape that is generally perpendicular to the axis A1. In the example shown, the bottom wall 22, is nevertheless slightly rounded with a concave face facing downwards. More precisely, in the example shown, the side wall 18 is constituted by a circular cylinder over a large fraction of its length along the direction of the axis A1. The ring 20 is connected via its bottom end to the remainder of the body of the container, specifically the side wall 18 in this example, by a zone referred to as the shoulder of the side wall 18.

For the container to be inspected correctly, it is appropriate to ensure that the container is presented in appropriate manner to the detector device 10. For this purpose, the device 10 of the invention has an installation zone on which the container is to be installed. This installation zone may be defined by an installation axis A'1 and an installation plane P defined as being a plane perpendicular to the installation axis A'1 and that could be a plane coinciding with the bottom end of the container (support surface of the container). Under such circumstances, a container moving in a direction perpendicular to its axis A1 has its bottom end traveling tangentially along the installation plane P. Thus, in order to be inspected correctly, the container needs to be presented in such a manner that its theoretical central axis A1 corresponds as closely as possible to the installation axis A'1, and that its bottom wall is presented above or level with the installation plane P, facing towards the device 10, while its open top end faces away from the device 10. Ideally, the two axes A1 and A'1 coincide. It can be understood that the entire device 10 of the invention may be positioned under the installation plane, while the container is located above the installation plane, without any risk of contacting the device. The container 14 can thus be conveyed using any movement in translation along a direction perpendicular to the installation axis A'1, without risk of interfering with the device 10.

In conventional manner, each container 14 is moved in translation by an automatic handling system, e.g. a conveyor (not shown but known per se) in order to bring the container into the installation zone in order to position it as accurately as possible in the installation zone so that the container has its theoretical central axis coinciding with the installation axis A'1, and then to extract the container from the installation zone. By way of example, the conveyor may be a conveyor having belts that support a container via its side face, or a conveyor that supports a container via its neck. Such containers leave the bottom and the insweep apparent from below.

The device and the method of the invention make use of a two-dimensional photoelectric sensor 24, also referred to as a matrix sensor and serving to acquire a two-dimensional image of the portion of interest 16 of the side wall 18 of the container. This matrix sensor may be incorporated in a camera, and by way of example it may be of the charge coupled device (CCD) type or of the complementary metal oxide semiconductor (CMOS) type. By way of example, the sensor 24 is constituted by a two-dimensional matrix of photoelectric elements. The sensor is generally associated with an electronic circuit for processing signals supplied by the photoelectric elements in order to deliver an analog or digital signal representative of the image received by the sensor. This signal representative of the image received by the sensor can then be delivered to an image processor device and/or to a display device and/or to an image storage device (not shown). The sensor 24 is generally associated with an optical conjugation system that transforms an arrangement of brightness in an object zone into an arrangement of brightness in an image zone, e.g. an optical objective system 26 that may include one or more optical means, in particular one or more refractive lenses and possibly also a diaphragm, that are associated in order to form an image of the sensor.

Advantageously, the device of the invention is compatible with the handling system for moving the container(s) in a direction perpendicular to their theoretical central axes A1. The handling system and the device of the invention may share a mechanical interface, for example they may both be mounted on a common frame or one may be fastened on a frame of the other. They may also advantageously be electronically interfaced. Thus, a system for controlling the handling system and an image processor device can advantageously exchange information in one direction or in both directions, either directly or via a central control device.

In a method of the invention, provision is made to use an optical element to form a plane image of the portion of interest of the wall of the container in the field of view of a matrix photoelectric sensor.

The device has an optical system 28 interposed between the container installation zone (A'1, P) and the sensor in order to form an image on the surface of the sensor 24 showing the portion of interest of the outer side wall of a container placed in the installation zone. The optical system has at least one optical element 30 that, in this example, is arranged between the objective system 20 and the installation zone. In the example shown, the optical system 28 between the sensor 24 and the installation zone thus comprises the objective system 26 and the optical element(s) 30.

The image that is formed on the sensor 24 is optically conjugated with the portion of interest 16 of the wall 18 of the container 14 by means of the optical system 28. As a result, light rays from a point under consideration of the portion of interest 16 of the wall 18 of the container 14 and having initial orientations that are different, while all being oriented so as to pass through the optical system 28, all become concentrated at a single point of the image formed on the sensor 24.

In the example shown in FIGS. 1, 2, and 4, the sensor 24, its objective system 26, the optical element 30, and the installation zone are in alignment in that order from top to bottom along the same installation axis A'1. The optical axis of the objective system 26 preferably coincides with the installation axis A'1. FIGS. 6 to 12 show another configuration in which the optical axis is not rectilinear, but rather segmented, e.g. by incorporating a deflector mirror in the objective system. Thus, a deflector mirror 32, inclined in this example at 45° relative to the installation axis A'1, is arranged on the optical axis between the sensor and the optical element, and more precisely between the objective system 26 and the optical element 30. The deflector mirror 32 thus defines a first segment A"1 of the optical axis beside the sensor 24 that is arranged at 90° relative to the installation axis A'1 and that then corresponds to the optical axis of the sensor and of the objective system 26, and a second segment, on the other side of the deflector mirror 32, which is arranged to match the installation axis A'1. As a result, it is possible to use the convention whereby the optical axis defines an optical axis or an optical axis segment in the installation zone and defining the installation axis A'1.

In an embodiment of the invention, the optical element 30 has a reflecting surface of revolution 31 around the installation axis A'1 and presents a minimum diameter that is greater than a maximum diameter of the portion of interest of the outer side wall of a container suitable for being received in the installation zone.

Preferably, the optical element 30 has a reflector or mirror forming the reflecting surface of revolution 31 that is downwardly flared, coaxial about the installation axis, and interposed between the installation zone and the sensor 24, the reflector presenting a minimum diameter that is greater than a maximum diameter of the portion of interest 16 of the outer side wall 18 of a container suitable for being received in the installation zone. In the embodiment shown, the reflector is frustoconical, and the reflecting surface is thus concave in a plane perpendicular to the installation axis A'1. In a variant, the reflecting surface of the optical element need not be frustoconical, but could rather be a surface of revolution presenting double curvature, being flared and generating by sweeping a segment of a non-straight curve around the installation axis A'1, e.g. a segment of a parabola, a hyperbola, or an ellipse. By way of example, in a radial plane, such a surface may present a profile that is concave or convex, while conserving its concave profile in a plane perpendicular to the installation axis A'1.

In the examples shown, the optical axis 30 comprises a frustoconical optical mirror 31 that is preferably made on the inside face of an annulus. The optical mirror 31 thus presents a frustoconical surface of revolution about the axis of symmetry of the installation axis A'1. The axis of symmetry of revolution of the optical mirror 31 may define the installation axis A'1. The optical mirror 31 presents an angle of inclination relative to the optical axis such that the large diameter of the optical mirror 31 is situated below its small diameter. The optical mirror 31 thus possesses an angle of inclination • considered in a radial plane relative to the vertical V parallel to the installation axis A'1 that corresponds to the half-angle at the apex of the truncated cone. The optical mirror 31 presents a height h and a small inside diameter d level with its small base. It should be considered that the optical mirror 31 is adapted to give the photoelectric sensor 24 a peripheral field of view C over 360° around the installation axis A'1. This peripheral field of view, facing towards the installation axis from the optical mirror 31 is defined between two cones C1 and C2 having the installation axis as their axis of symmetry. The two cones C1 and C2 are axially offset in the installation zone, they flare downwards, each having its apex in the installation zone, and they may present tapers that are different. The wider-open cone C1 passing via the large diameter of the reflecting surface 31 is arranged below the cone C2 passing via the small diameter of the reflecting surface 31. C1 and C2 do not intersect inside the diameter defined by the optical mirror. As a result, the field of view of the sensor 24 through the optical system downstream from the optical mirror 31 presents a field angle • that is divergent in the example shown from the optical mirror 31. This enables the sensor 24 to observe the portion of interest 16 of the outer side wall 18 of the container and to observe the portions in relief 12 arranged on this portion of interest 16.

In addition, the optical mirror 31 is adapted to present an observation angle • in elevation for collecting the light rays reflected by the portions in relief 12. The observation angle • may be defined in a radial half-plane containing the installation axis A'1 and defined by that axis between a plane perpendicular to the installation axis A'1 and a mean observation direction from the optical mirror 31. This mean observation direction may correspond to a mean direction between the two limiting cones C1 and C2, i.e. a direction bisecting the angle formed by these cones in a radial half-plane. It should thus be considered that the field of view of the sensor through the optical system 28 downstream from the optical mirror depends in particular on the size of the sensor and on the focal length of the objective lens, and also on the diameter d, the angle of inclination •, and the height h of the optical mirror 31. The field of view through the optical mirror 31 has an influence on the extent (in the direction of the installation axis) of the portion of interest of the side wall that is seen by the sensor through the optical system 28.

In other embodiments of the invention, the optical element may be made not in the form of a reflecting cone but in the form of a prism, in particular a refracting prism of annular shape, or a Fresnel lens, creating a field of view analogous to that described above.

Figure 13:
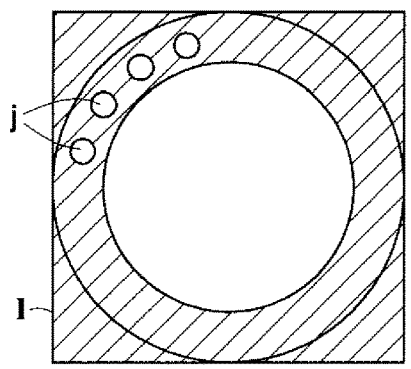
FIG. 13 shows, by way of example, an image I as might be formed by the sensor of a device of the invention or with the help of a method of the invention.

Because of the field of view as created in this way for the sensor 24, the sensor is capable of looking through the optical system 28 and in particular the optical element 30, to observe the insweep of a container installed appropriately in the installation zone, in the form of an image that is formed in the plane of the sensor 24 that is perpendicular to the optical axis, even though the outside surface of the insweep on the container is a surface that is parallel to the installation axis extending the optical axis in the installation zone, or a surface that forms an acute angle in the vicinity of the portions in relief that is greater than 45° relative to a plane normal to the installation axis. The optical element 30 thus transforms a three-dimensional surface into a plane surface on the plane of the sensor. By way of example, FIG. 13 shows an image I that might be received by the sensor 24. The received image I shows an annulus in the plane of the sensor corresponding to the insweep, and within which there can be seen information j corresponding to respective portions in relief 12. Nevertheless, the image formed in the plane of the sensor by the optical system 28 can be perceived by the photoelectric sensor 24, and thus transformed into an image signal, only insofar as at least a portion of this received image is illuminated. This illumination assumes that light rays are reflected by specular reflection on the portion of interest 16 of the side wall 18 that is in the field of view of the sensor.

In an aspect of the invention, the method makes provision for lighting a portion of interest of the outer side wall of the container that is limited in the direction of the installation axis A'1, but that extends over 360° around the installation axis A'1, by using at least one main light source 34 supplying a peripheral incident light beam made up of radial light rays contained in a radial plane containing the installation axis, said radial light rays being directed towards the installation axis, and the beam including non-parallel radial rays in a common radial plane.

Thus, in parallel, a device of the invention includes for this purpose a lighting system including at least one main light source 34 that is peripheral and that has the installation axis as its own axis, and that is suitable of supplying such a peripheral incident light beam in the installation zone.

The radial rays are preferably directed towards the installation axis A'1 without necessarily being perpendicular thereto. On the contrary, as shown in FIG. 2, it is shown that the peripheral incident light beam may contain radial rays that form an angle with a plane perpendicular to the installation axis A'1, which angle preferably lies in the range 0 to 45 degrees. Preferably, the light beam contains radial rays over an angular spread that is continuous or substantially continuous in a radial plane. This spread may have an annular extent of at least 30 degrees, or possibly more, starting from a point of the main light source 34. The rays contained in this spread may form an angle lying in the range 5 degrees to 40 degrees relative to a plane perpendicular to the theoretical central axis. The light beam delivered by the main source 34 is a beam that needs to be adapted to light the portion of interest 16 of the side wall of a container that is to be inspected. The light spread of the source in a radial plane should thus be adapted to meet this constraint. Apart from the nature of the main light source 34 (diodes, optical fibers, fluorescent tubes, etc. . . . ), which may determine the extent of this spread to some extent, the main light source may include one or more masks and/or one or more reflectors, as described in Document EP 1 010 126, and/or one or more refracting prisms for limiting or expanding the spread of light emitted in a radial plane. It may be observed at this point that any light rays emitted by the light source in planes that are not radial are not taken into consideration. Nevertheless, it may be advantageous to use a light source in which the magnitude of non-radial rays, i.e. rays that are not contained in a radial plane, is reduced. In the limit, it is possible to envisage lighting the portion of interest 16 with a peripheral beam that is purely radial, and comprises radial light rays only. In general manner, the main light source may be identical or similar to the source described in Document EP 1 010 126, to which reference may usefully be made.

The light source 34 presents a diameter greater than the diameter of the portion of interest of the side wall of containers that are to be inspected using the device. This annular light source 34 is arranged below the installation zone, and thus below the portion of interest of the side walls of containers. In a radial half-plane containing the installation axis A'1 and defined by the installation axis A'1, the annular light source 34 corresponds to a source that may be a point source, or on the contrary that may have a certain extent in this half-plane, as shown in the figures. Preferably, the main source 34 is seen from a point of the portion of interest of the side wall of the container over a viewing angle that is less than 15 degrees, preferably less that 5 degrees.

In the example shown of the invention, it may be observed that:

the lighting system, including the main light source 34, the sensor 34;

the sensor 24; and the optical system 28 including the optical element 30 and its reflecting surface 31;

are arranged below the installation zone, and therefore do not interfere with the path of containers if they are moved perpendicularly to the installation axis A'1, and regardless of the orientation of that path in a plane perpendicular to the axis A'1.

A method and a device as described above seek to make use of the fact that the incident light beam is reflected at least in part by specular reflection on the portion of interest of the outer side wall and on its portions in relief, and that at least some of the rays of the beam that are reflected are picked up via the optical system 28 on the sensor 26. Nevertheless, in order to ensure that the device of the method operates as well as possible, it is necessary to ensure that the optical system 28 picks up only, or mostly, light rays reflected by the portions in relief 12, and on the contrary picks up as few as possible of light rays reflected by zones of the portion of interest 16 that are adjacent to the portions in relief 12.

A method of the invention may include a step that consists in processing the image received by the sensor in order to detect the portions in relief. Such image processing may be performed by an image processor device, in particular a computer device, that may optionally be integrated in a device of the invention or that may be electronically interfaced with the device of the invention, or that may be distinct from the device. Under such circumstances, data corresponding to the image signals delivered by the sensor 24 is transferred by conventional means to the processor device.

FIGS. 2 and 3 show an example of a path followed by a light ray emitted by the main light source 34, reflected by a portion in relief 12 of a container in a direction such that the reflected ray is picked up by the optical system 28, by reflection on the optical element 30, and is thus directed onto the sensor 24 so as to form a light point of an image on the sensor. In FIG. 3, there can be seen in particular a ray i1 emitted by the main light source 34 towards a portion in relief 12 in a radial plane. There can also be seen a ray i2 emitted by the main light source 34 in a radial plane and striking the portion of interest 16 of the outer side wall 18 beside a portion in relief, in this example above a portion in relief along the direction of the installation axis A'1. In this example, since the container 14 presents an insweep that is straight, the normal n2 of the point of impact P2 of the ray i2 is substantially perpendicular to the installation axis A'1, such that the ray i2 is reflected by specular reflection on the outside surface of the side wall 18 in the form of a reflected ray ir2 that is upwardly directed, i.e. away from the device of the invention, and is thus not received by the sensor 24 through the optical system 28. On the contrary, the ray i1 emitted by the main light source 34 impacts the portion in relief 12 at a point P1 of the portion in relief 12 having a normal n1 relative to the surface of the portion in relief 12 at the point P1 that is directed downwards, such that the ray i1 is reflected in the form of a ray ir1 towards the optical element 30, which in turn reflects this ray by specular reflection in the form of a ray irr1 towards the sensor 24 through the optical objective system 26. Thus, the zone of the sensor 24 corresponding to the point P1 is illuminated so that the sensor delivers an image in which this point appears bright.

FIG. 3 also shows the situation of a ray coinciding with the ray i'1 but impacting the side wall 18 in the absence of a portion in relief 12. Under such circumstances, given the shape of the portion of interest of the outside surface 18 in the immediate vicinity of the portion in relief 12, it can be seen that such a ray would be reflected along a ray i'r1, substantially like the ray ir2, i.e. upwards away from the device of the invention, and would thus not be received by the sensor 24 through the optical system 28.

It should be observed that FIG. 2 and FIG. 3 show the situation in a given radial plane in which there is a portion in relief 12 in the portion of interest 16 of the side wall 18. Since the system under consideration including the device and the container is circularly symmetrical about the installation axis A'1, adjacent portions of the system situated in radial planes that are very slightly offset angularly around the installation axis A'1 on either side of the radial plane shown in FIG. 3 are adjacent portions in which the portion in relief 12 is not present. Thus, in these adjacent portions, the reflection along the ray ir1 towards the optical element 30 does not take place, since there is no portion in relief. In these adjacent portions, none of the rays emitted by the main light source 34 are reflected towards the sensor 24 through the optical system 28 including the optical element 30. As a result, the image of these adjacent portions on the photoelectric sensor 24 is not illuminated, such that the sensor delivers an image in which these zones appear dark.

It can thus be understood that the device of the invention makes use of the particular shape of the portion in relief 12 relative to the shape of the zones adjacent to this portion in relief in the portion of interest 16 of the side wall 18. By definition, these portions in relief present an outside surface with considerable general curvature and thus present a wide variety of normal directions when considering each of the points of the surface of a portion in relief. This maximizes the probability that a ray emitted by the main light source 34 strikes one of these points with a direction of incidence such that the reflected ray is directed towards the optical element 30 and is thus subsequently directed by the remainder of the optical system 28 to the sensor 24. In contrast, outside the portions in relief, the portion of interest 16 of the outer side wall 18 presents a shape that is relatively uniform in the sense that two points that are close together in the portion of interest 16, outside the portions in relief 12, present normals at orientations with little difference. As a result, under favorable circumstances, the normal at a point of this portion of interest 16, outside the portions in relief 12, is generally oriented in such a manner that rays it reflects are not directed towards the optical element 30, and thus not towards the sensor. Thus, under such circumstances, light contrast results in the image received by the sensor 24 between the image points that, like the point P1 of the portion in relief, reflect light towards the sensor 24 through the optical system 28 and those that, like the point P2 adjacent to the portion in relief, reflect light in some other direction. This brightness contrast in the image received by the sensor 24 gives rise, in the image signal delivered by the sensor 24, to contrast that can easily be used by an image processor device in order to identify the presence of a portion in relief and its location on the portion of interest 16 of the side wall 18.

FIGS. 2 and 3 show a relatively ideal configuration in which such contrast is obtained when the optical element 30 and the main light source 34 are in the respective positions shown in the figures. Nevertheless, for certain shapes of container, presenting portions in relief of different shapes and/or presenting insweeps of different shapes, e.g. insweeps that are rounded or steeply inclined in the vicinity of the portions in relief, as shown in FIGS. 4 and 5, it has been found that such contrast between the portions in relief and the adjacent zones of the insweep is not obtained or is obtained insufficiently, for these respective positions of the optical element 30 and of the main light source 34. This can result from the fact that none of the light rays emitted by the main light source are reflected by the portion in relief towards the optical element 30, and/or by the fact that both rays reflected by the portion in relief and also rays reflected by the zones adjacent to the portion in relief are directed towards the optical element 30 and thus towards the sensor 24. In both of these configurations, an image is obtained on the sensor does that not make it possible to obtain brightness contrast between the zones corresponding to the portions in relief and the zones adjacent to the portions in relief. Both of these types of zone are thus illuminated, or else they are both black, but in any event they are not distinguishable by a processor device, or they cannot be discriminated between sufficiently.

Thus, in an aspect of the invention, provision is made to cause the main light source 34 delivering the peripheral incident light beam to move in translation along the direction of the installation axis A'1 relative to the optical element 30 in order to modify the contrast of the image seen by the sensor 24 between zones of the image corresponding to the portions in relief 12 and zones of the image corresponding to the remainder of the portion of interest 16 of the wall of the container.

For this purpose, the main light source 34 supplies a peripheral incident light beam that is movable in translation along the direction of the installation axis A'1 relative to the optical element 30.

By means of such a provision, for a given point P1 of a portion in relief and a given point P2 belonging to a zone adjacent to this portion in relief, the movement of the main light source 34 causes these points to be illuminated with different angles of incidence so they reflect incident rays in different directions compared with the directions corresponding to the initial position of the main light source 34. It is thus possible to vary the direction of these reflected rays and to find a position for the light source 34 in which there is sufficient contrast between firstly the image on the sensor 24 as seen through the optical device 28 including the optical element 30 of a light point P1 belonging to the same portion in relief 12, and secondly the image on the sensor 24 as seen through the optical device 28 including the optical element 30 of points P2 belonging to a zone adjacent to that portion in relief on the portion of interest 16 of the side wall 18.

In other words, if consideration is given to a portion in relief 12 for which the vicinity has an orientation such that the rays coming from the source 34, when the source 34 is in an initial position, are reflected towards the optical element 30, moving the source in translation along the installation axis A'1 enables the angle of incidence of the light on each point P2 in the vicinity of the portion in relief to be changed. As a result, after traveling a certain distance, this movement can make it possible to obtain an angle of reflection for this light on each of these points P2 that is such that the light is no longer deflected towards the optical element 30. Meanwhile the shape of the portion in relief 12 ensures that there is some other point on the portion in relief 12, very close to the point P1, but having a normal oriented very differently from the normal at P1, which will direct light towards the optical element 30. In this position of the source 34, the portion in relief 12 can be seen as being pale on a dark background corresponding to the zone adjacent to the portion in relief.

FIGS. 4 and 5 show the configuration of a bottle having an insweep in the portion of interest 16 that is highly inclined relative to the theoretical central axis A1, in which configuration it is found for at least certain shapes of the portions in relief, that a very different position of the main light source 34 enables much better contrast to be obtained in the image received by the sensor 24 between the zones corresponding to the portions in relief and the zones adjacent to those portions in relief. FIGS. 4 and 5 use the same references relating to the various rays between the main light source 34 and the sensor 24 so as to correspond to the description given for the configuration of FIGS. 2 and 3. It should be observed that in the configuration shown in FIGS. 2 and 3, the main light source 34 in its optimum position is arranged above the optical element along the direction of the installation axis A'1. In contrast, in FIGS. 4 and 5, the main light source 34 in its optimum position is arranged below the optical element 30 along the direction of the installation axis A'1. It can thus be seen that it can be advantageous to move the main light source 34 over a certain adjustment range between two extreme positions.

Advantageously, a method of the invention may include a step of optimizing the movement of the main light source 34 that consists in searching for at least one position of the source along the direction of the installation axis A'1 relative to the optical element 30 in which a level of light contrast between the zones of the image corresponding to the portions in relief and zones of the image corresponding to the remainder of the portion of interest of the wall of the container, in particular corresponding to the zone adjacent to the portion in relief 12, is greater than a predetermined level. This predetermined level of contrast may be a level that is constant or it may be variable, in particular a level that is variable as a function of various parameters that may be associated with the device 10 and/or with the container 14.

Provision may also be made for such an optimization step to be automated. For example, the source may be moved by automatic shifter means controlled by a central control unit. The central control unit controls the movement means while acting, for some number of positions of the main light source 34 relative to the optical element 30, to analyze the light contrast in the images that are obtained, until finding an optimum position for the light source 34 that gives good contrast in the image between the zones corresponding to the portions in relief and the adjacent zones. Naturally, such an optimization step could be performed manually by an operator preferably, having viewing means, e.g. on a computer screen, for viewing the image signal delivered by the sensor 24. Such an operator can then search the adjustment range for an optimum position of the light source 34 in which the image can easily be interpreted by an image processor device.

In general manner, provision may be made for the main light to be movable between a multitude of distinct blocked positions along the direction of the installation axis, the blocked positions lying between two extreme positions. There are thus at least two blocked positions for the main light source 34 relative to the optical element 30, e.g. corresponding to the extreme positions, and preferably there are at least three blocked positions, in particular including at least one intermediate blocked position between the two extreme positions.

These blocked positions of the light source 34 may be discrete positions predefined relative to the optical element 30. In another embodiment, the main light source 34 may be blockable in any position relative to the optical element 30 between two extreme positions.

The device 10 preferably includes control means for controlling the movement of the main light source 34 in translation along the direction of the installation axis relative to the optical element 30. These control means may be means that are mechanical, hydraulic, electrical, magnetic, etc. The control means are advantageously motor driven. They may be associated with means for guiding the light source 34 in translation relative to the optical element 30.

Preferably, the device 10 has means for blocking the main light source in its blocked positions relative to the optical element. Advantageously, the blocking means are mechanical blocking means, e.g. by clamping or by co-operation between shapes.

FIGS. 6 to 8 show diagrammatically a device in accordance with the invention enabling the method of the invention to be performed. The device 10 comprises a base 40 that is to form an element of the device that is stationary in operation and that may for example be secured relative to a container conveyor line. For example, the base 40 may be fastened to a frame, itself connected to the conveyor installation. The frame may be the frame of an inspection station associated with a conveyor line. By way of example, the base 40 is in the form of a plate arranged in a plane perpendicular to the installation axis A'1, and thus specifically a plate that is to be arranged in a horizontal plane. In the example shown, the plate is substantially square in shape. On a front side of the square, the base 40 has two guide columns 42, e.g. arranged close to the side ends of the front side, and extending along a vertical direction parallel to the direction of the installation axis.

The device 10 also has a primary carriage 44 that carries the conical element 30.

In an advantageous embodiment, the primary carriage 44 carrying the optical element 30 is movable in translation relative to the base 40 along the direction of the installation axis so as to enable the optical element 30 to be moved relative to the direction along the installation axis, and thus relative to any container arranged in the installation zone. Specifically, the device may be used with containers of shapes that are different, in particular in terms of the position, the height, and the diameter of the portion of interest. Instead of possibly needing to adapt a conveyor line in order to bring the containers into a favorable position relative to the device, it can be much easier to provide the optical element 30 with this ability to move so as to be capable of causing the peripheral field of view C in which the sensor 24 can observe the portion of interest 16 of the side wall 18 of the container through the optical system 28 of which the optical element 30 forms a part to be brought into coincidence with the portion of interest 16 that it is desired to observe. In other words, the optical element is movable relative to the installation zone along the direction of the installation axis in order to bring the portion of interest 16 of the wall of the container into the field of view of the matrix sensor as seen through the optical system 28 including the optical element 30.

This ability of the optical element 30 to move relative to the base 40 and thus relative to a given container in position in the installation zone can be combined with the ability of the optical element 30 to move relative to the sensor 24. It is thus possible to make provision for the optical element 30 to be movable relative to the sensor 24 along the direction of the installation axis A'1. Under such circumstances, the photoelectric sensor 24 may for example be mounted on the base 40. Since the optical element 30 is then mounted on the primary carriage 44 that is movable relative to the base 40, it becomes possible to move the optical element 30 relative to the sensor 24.

Nevertheless, in the embodiment shown in FIGS. 6 to 12, the optical element 30 has a position that is stationary relative to the photoelectric sensor 24. More particularly, they may be mounted on the same primary carriage 44. Since this primary carriage 44 is movable relative to the base 40, and thus relative to the reception zone and to a container arranged in the reception zone, it is possible, by moving the primary carriage 44, to move the field of view C in which the sensor 24 observes the installation zone via the optical element 30.

In the example, the primary carriage is guided on the columns 42. Its movement is controlled by a manual mechanism having a control lever 46 with one end pivotally mounted about a lateral axis A2 perpendicular to the installation axis of the base 40. The lever 46 co-operates with a control rod 49 of lateral axis A3 parallel to the axis A2, the control rod 49 being connected to the primary carriage 44. Provision may be made for the control rod 49 to be slidably mounted relative to the lever 46 along the direction of the lever, or for it to be slidably mounted along a direction perpendicular to the axis A3 and to the installation axis relative to the primary carriage 44 in order to avoid the control system being statically undetermined. In the diagram of FIG. 7, there can be seen the situation in which the lever 46 can slide in the control rod 49. It can thus be understood that, by pivoting the lever 46 about its axis 42 relative to the base 40, the intermediate carriage 44 is caused to move vertically, and thus the optical element 30 is caused to move along the direction of the installation axis relative to the base 40. Blocking means, e.g. operating by clamping or by mechanical blocking, are provided to enable the intermediate carriage to be blocked relative to the base 40. Preferably, provision is made to enable the primary carriage 44 to be blocked in a multitude of blocked positions. These positions may be discrete. Alternatively, the intermediate carriage 44 may be blocked in any of its positions between two extreme positions, namely a high position and a low position.

In the example shown, both the optical element 30 and the photoelectric sensor 24 are carried by the intermediate carriage 44 and are thus in positions that are relative to each other, while being movable relative to the base.

The primary carriage 44 may include a bottom tray 48 and a top tray 50 that are spaced apart along the direction of the installation axis and that extend substantially in planes perpendicular to the installation axis, and each presenting, in the example shown, a shape that is substantially square or rectangular. The top tray 50 carries an annular ring supporting the optical element 30, and as a result it has a central opening that corresponds at least to the large diameter of the optical element 30, which is represented in the figure by a frustoconical reflector, having its concave inside surface forming the reflection surface situated on the installation axis and flaring downwards. In the example shown, the truncated cone of the optical element 30 is arranged above the top tray 50.

The bottom tray 48 carries the photoelectric sensor. In the embodiment shown, the optical system has a deflector mirror 32 arranged at 45°, which mirror is thus installed substantially at the center of the bottom tray 48 so as to form an image A"1 of the installation axis A'1 that extends at 90° to the installation axis in a front direction. In the example shown, the reflection mirror 32 is a plane mirror that is parallel to the lateral axes A2 and A3 of the system for controlling movement of the intermediate carriage. In order to obtain an optical path of sufficient length for the optical system 28, the sensor 24 and its objective system 26 are mounted on a front extension 52 of the bottom tray 48 of the intermediate carriage. In the example shown in particular in FIG. 8, the photoelectric sensor 24 and the objective system 26 are adjacent to a box 54 that may contain an electronic circuit for processing signals supplied by the photoelectric elements in order to deliver a signal representative of the image received by the sensor. The box includes a connector for connecting the sensor 24 to an image processor device (not shown), e.g. via a wired connection 56.

In the example shown, the trays 48 and 50 of the intermediate carriage 44 are connected to each other by a front wall 58, in particular in order to maintain the spacing between the two trays along the direction of the installation axis. By way of example, the front wall 58 extends in a plane perpendicular to the front axis, level with the two guide columns 42. It is thus provided with a window 60 to pass the light path between the objective system 26 and the deflector mirror 32. In reality, provision may be made for the carriage 44 also to have side walls and a rear wall (not shown) so as to form a closed box protecting the optical system 28 from dust and interfering light. The camera may also be protected by a box, as shown in FIG. 6.

The device 10 of the invention also has a secondary carriage 62 that is arranged above the primary carriage 44, in particular above the top tray 50 and its frustoconical optical element 30, and that carries the main light source 34. By way of example, the secondary carriage 62 may be in the form of a tray of square shape that is substantially perpendicular to the installation axis A'1. The tray of the secondary carriage 62 is pierced in its center by an opening of large size for passing the field of view C. By way of example, the main light source 34 is formed by a series of diodes, e.g. arranged in an annular housing formed in the top surface of the secondary carriage 62. The diodes are arranged in a circle around the installation axis A'1. All of them may face radially towards this axis with an angle of inclination relative to the axis. They light the portion of interest 16 of the side wall 18 of the container 14.

As mentioned, the secondary carriage 62 is movable relative to the primary carriage 44 so as to be capable of moving the main light source 34 relative to the optical element 30. In the example shown, the secondary carriage 62 is also guided to move in translation on the guide column 42. In order to control the movement of the secondary carriage 62 relative to the primary carriage 44, movement control means are provided that may for example be in the form of a rocker 64 having one end connected to the top tray 50 of the primary carriage 44 via a first pivot connection about a first front axis A4 perpendicular to the installation axis, and having a second end connected to the secondary carriage 62 via a second pivot connection about a second front axis A5 parallel to the first front axis A4, with at least one of the two pivot connections, and preferably the pivot connection with the secondary carriage 62, also being capable of moving along a lateral axis perpendicular to the installation axis and to the front axis in question. The rocker 64 has a control arm 66 that is substantially perpendicular to a front axis and to the direction interconnecting the two front axes A4 and A5. The free end of the control arm 66 has a grip handle 68 enabling the rocker 64 to be manipulated and caused to pivot relative to the front axis A4, thereby causing the secondary carriage 62 to move relative to the primary carriage 44. This serves to control the movement of the main light source 34 along the direction of the installation axis relative to the optical element 30.

In this embodiment, blocking means are provided for blocking the secondary carriage 62 in a series of predefined discrete positions relative to the primary carriage 44. In the embodiment shown, blocking is performed by co-operation between shapes. To do this, it can be seen that the free end of the control arm 66 moves over a circular arc relative to the front axis A4 in front of the front wall 58 of the primary carriage. This front wall 58 is provided with a series of depressions 70, e.g. of cylindrical or conical shape about front axes, that are arranged in a circular arc around the front axis A4. The control arm 66 has a plunger directed along a front axis towards the front surface, the plunger being capable of becoming blocked in any one of the depressions 70 in order to block the control arm 66 relative to the wall 58 and thus block the position of the secondary carriage 62 along the installation axis A'1 relative to the primary carriage 44. In order to pass from one position to another, the plunger is disengaged elastically from one depression 70 and moves to another conical depression. The elasticity may be provided for example by the resilience of the control arm 66 in a frontal direction, or by providing a resilient mount for the plunger on the control arm 66 along the direction of the front axis.

Alternatively, the plunger may be formed by one end of the grip handle 68 that is mounted to pass through the free end of the arm 66. The handle 68 can then be movable along the direction of the front axis relative to the control arm 66 and urged elastically towards the front surface while leaving it possible, by applying a traction force in the opposite direction, to separate the plunger from a depression 70 so as to allow the control arm 66 to move, thereby moving the main light source 34 relative to the conical element 30.

It can be understood that in the device of the invention, the means for moving the optical element 30 relative to the base 40 are not essential since, by way of example, it is possible for the same function to be performed by positioning containers differently in the installation zone depending on their shape. Nevertheless, in the presence of such means, it is advantageous to make provision for the means for moving the main light source 34 relative to the optical element 30 to be capable of operating independently of the means for moving the optical element 30 relative to the base 40. Thus, it is possible to modify the orientation of the lighting relative to the field of view C of the sensor 24 without moving the field of view relative to the container.

Thus, while the device is in use, provision may be made for a step of moving the optical element 30 along the direction of the installation axis A'1 in order to bring the image of the portion of interest 26 of the wall of the container 18 into the field of view of the matrix sensor 24, and a step consisting in moving the main light source 24 relative to the optical element 30, which can then be performed after the step of moving the optical element 30.

In contrast, and by construction, in the example shown, the means for controlling the movement of the optical element 30 leads to simultaneous movement of the light source 34 together with the optical element relative to the base 40. Specifically, this results from the fact that the secondary carriage 62 is free to slide relative to the base 40 while it is connected to the primary carriage 44 by the rocker 64 that sets the relative position between the secondary carriage 62 and the primary carriage 44, and thus between the main light source 34 and the optical element 30. Thus, a movement of the primary carriage 44 relative to the base 40 gives rise to an equal movement of the secondary carriage 62 relative to the base 40, and thus relative to the installation zone.

In the example shown, the secondary carriage 62 also carries a top plate 71 of transparent glass that is to protect the device 10 as a whole from any debris coming from above, while passing both the field of view of the sensor 24 and the light beam generated by the lighting system.

In the example shown, and in particular in FIG. 8, the secondary carriage 62 is shown in its lowest position relative to the primary carriage 44. It can be seen that in this position, the main light source 34 is substantially at the same height as the optical element 30, or even above it.

Thus, the device 10 shown in FIGS. 6 to 8 enables the main light source 34 to move over only a certain range of positions between two extreme positions, this range being organized in general manner between the optical element 30 and the installation zone, i.e. above the optical element 30. This adjustment range is the preferred adjustment range making it possible to obtain satisfactory contrast in the image received by the sensor between the image zones of portions in relief and the image zones of zones adjacent to the portions in relief. Nevertheless, as described with reference to FIGS. 4 and 5, in certain circumstances corresponding to containers of particular shapes, it can be necessary for the peripheral incident light beam to be generated by a light source situated below the optical element 30. It would then naturally be possible to provide a device in which the main light source is movable relative to the optical element 30 along an extended range of positions covering all the necessary positions, including positions situated opposite from the installation zone relative to the optical element 30, i.e. below the optical element 30. Under such circumstances, the main light source 34 would be movable between at least two extreme positions along the direction of the installation axis, these extreme positions being on respective opposite sides of the axial position of the reflection surface 31 of the optical element 30.

Nevertheless, insofar as such shapes are atypical shapes, it may be more suitable in those situations to make provision for an auxiliary light source 72 that is offset from the main light source 34 along the direction of the installation axis, and that is suitable for supplying an auxiliary peripheral incident light beam that is different from the main beam supplied by the main light source 34, the auxiliary beam having radial rays contained in a radial plane containing the installation axis A'1, said radial rays being directed towards the installation axis A'1, and the auxiliary beam comprising non-parallel radial rays in a common radial plane.

The two light sources 34 and 72 should preferably be used in alternation, rather than simultaneously.

Such an auxiliary light source 72 that is annular about the installation axis A'1 is shown in FIG. 8. It is arranged below the optical element 30 and it is carried by the top tray 50 of the primary carriage 44. This auxiliary light source 72 is not movable relative to the optical element 30 and it is thus stationary relative thereto.

Thus, in this device, the main light source 34 is movable between at least two extreme positions along the direction of the installation axis A'1 both of which extreme positions may be on one side of the axial position of the reflection surface of the optical element 30, while the auxiliary light source 72 may be arranged on the other side of the axial position of the reflection surface 31.

Advantageously, a device as described above enables portions in relief 12 carried by the portion of interest 16 of an outer side wall 18 of a container 14 to be read, even when zones adjacent to the portions in relief 12 in the outside surface 18 of the portion of interest 16 present a normal that may be at an angle of as much as 45°, relative to a plane normal to the installation axis A'1, but that is preferably less than 45°.

FIGS. 9 and 10 are diagrammatic views of the device seen in the lateral direction, showing how it is possible in a device of the invention to move the optical element 30, specifically by moving the entire primary carriage 44 carrying the sensor 24 and the optical system 28 incorporating the optical element 30, for the purpose of bringing the field of view of the sensor 24 into a position in which it can see the portion of interest 16 of the side wall 18 of the container, as shown in FIG. 10.

FIGS. 11 and 12 are diagrammatic views of the device seen in the front direction. FIG. 11 shows the same position of the device 10 as FIG. 10, but from a different viewpoint. FIG. 12 shows the secondary carriage 62 being moved to enable the direction of incidence of the peripheral light beam L on a given point of the portion of interest 16 to be modified without moving the field of view. It can be seen clearly that during the movement of the light source 34, it is not the emission direction of the peripheral light beam from the main light source 34 that is modified, since the main light source is moved in translation. On the contrary, the modification is indeed to the angle of incidence of the rays coming from the source, as seen from a point under consideration of the portion of interest of the side wall 18 of the container, resulting from the movement of the source.

In a preferred application of the invention, the device and the method are used for reading portions in relief, e.g. beads, on a bottle made of transparent glass, the portions in relief being arranged on the insweep of the bottle and forming a code corresponding to a number of the mold used for fabricating said bottle.

The invention is not limited to the examples described and shown since various modifications can be made thereto without going beyond the ambit of the invention.

The invention claimed is:

1. A method of optically reading portions in relief forming an identification code, the portions in relief (12) being carried by an outer side wall (16) of a container (14) having a theoretical central axis (A1), the method being of the type comprising the steps of:
    using a light source to light a portion of interest (16) of the outer side wall (18) of the container (14), which portion extends around the theoretical central axis (A1), the light source supplying a peripheral incident light beam comprising radial light rays contained in a radial plane containing the theoretical central axis (A1), and the beam including non-parallel radial rays in a common radial plane;
    using at least one optical element (30, 31) to form a plane image of the portion of interest of the wall of the container in the field of view of a two-dimensional photoelectric sensor (24);
    processing the image received by the sensor (24) in order to detect the portions in relief (12);
    the method being of the type in which the incident light beam is reflected at least in part by specular reflection on the portion of interest (16) of the outer side wall (18) and on the portions in relief (12);
    the method further comprising causing the light source supplying the peripheral incident light beam to move in translation along the direction of the theoretical central axis (A1) relative to the optical element (30, 31) in order to modify the contrast in the image received by the sensor (24) between zones of the image corresponding to the portions in relief (12) and adjacent zones of the image corresponding to zones of the portion of interest (16) of the wall (18) of the container (14) that are adjacent to the portions in relief (12).

2. A method according to claim 1, further comprising a step of optimizing the movement of the source (34), by searching for at least one position of the source along the direction of the theoretical central axis (A1) relative to the optical element (30) in which contrast between the zones of the image corresponding to the portions in relief (12) and adjacent zones of the image corresponding to zones of the portion of interest (16) of the wall (18) of the container (14) that are adjacent to the portions in relief is at a level that is greater than a predetermined level.

3. A method according to claim 1, further comprising a step of moving the optical element (30) along the direction of the installation axis in order to bring the portion of interest (16) of the wall (18) of the container (14) into the field of view of the sensor (24), and in that the step causing the main light source (34) to move relative to the optical element (30) is performed after the step of moving the optical element (30).

4. A method according to claim 1, wherein in a radial plane containing the theoretical central axis (A1), the light source (34) is seen from a point of the portion of interest (16) of the side wall (18) of the container (14) at a viewing angle of less than 15 degrees, preferably less than 5 degrees.

5. A method according to claim 2, wherein the step of optimizing the movement of the source is automated.

6. A device (10) for optically reading portions in relief (12) carried by a portion of interest (16) of an outer side wall (18) of a container (14), the device comprising a container installation zone having an installation axis, and further comprising:
    a two-dimensional photoelectric sensor (24);
    an optical system (28) interposed between the container installation zone and the sensor (24) in order to form on the sensor (24) an image of the portion of interest (16) of the outer side wall (8) of a container (14) placed in the installation zone, the optical system (28) including at least one optical element (30) having a reflection surface of revolution (31) around the installation axis (A'1) and presenting a minimum diameter greater than a maximum diameter of the portion of interest (16) of the outer side wall (18) of a container susceptible of being received in the installation zone;
    an optical axis defined by the optical system (28) and extending in the installation zone in order to define the installation axis (A'1); and
    a lighting system including at least a main light source (34) that is peripheral and has the installation axis (A'1) as an axis thereof, and that is suitable for supplying a peripheral incident light beam in the installation zone, the beam comprising radial rays contained in a radial plane containing the installation axis (A'1), said radial rays being directed towards the installation axis (A'1), and the beam comprising non-parallel radial rays in a common radial plane;
    wherein the lighting system (34), the sensor (24), and the optical system (28) are arranged below the installation zone; and
    further wherein the main light source (34) supplying the peripheral incident light beam is movable in translation along the direction of the installation axis (A'1) relative to the optical element (30).

7. A device according to claim 6, wherein the main light source (34) is movable between a multitude of distinct blocked positions along the direction of the installation axis (A'1), the blocked positions extending between two extreme positions.

8. A device according to claim 7, wherein the main light source is movable between a multitude of predefined discrete blocked positions relative to the optical element (30).

9. A device according to claim 6, wherein at least two positions for the main light source (34) are included relative to the optical element (30), and preferably at least three blocked positions.

10. A device according to claim 6, wherein the main light source (34) can be blocked in any position relative to the optical element (30) between two extreme positions.

11. A device according to claim 6, further comprising control means (64) for controlling the movement of the main light source (34) in translation along the direction of the installation axis (A'1) relative to the optical element (30).

12. A device according to claim 6, further comprising blocking means (70) for blocking the main light source (34) in blocked positions relative to the optical element (30).

13. A device according to claim 6, wherein the optical element (30) is movable relative to the photoelectric sensor (24) along the direction of the installation axis (A'1) for bringing the portion of interest (16) of the wall of the container into the field of view of the photoelectric sensor through the optical system (28).

14. A device according to claim 13, further comprising movement means (46) for moving the optical element (30) relative to a base (40) of the device, and in the movement means for moving the main light source (34) relative to the optical element (30) operate independently of the movement means (46) for moving the optical element (30) relative to the base (40).

15. A device according to claim 14, wherein the movement means (46) for moving the optical element (30) cause the main light source (34) to move simultaneously with the optical element (30) relative to the base (40).

16. A device according to claim 15, wherein the optical element (30) is secured to a primary carriage (44) that is movable relative to the base (40) along the direction of the installation axis (A'1), in that the main light source (34) is secured to a secondary carriage (62) that is movable relative to the primary carriage (44) along the direction of the installation axis (A'1), and in that a movement of the primary carriage (44) gives rise to an equal movement of the secondary carriage (62).

17. A device according to claim 6, wherein the main light source (34) is movable between at least two extreme positions along the direction of the installation axis (A'1), which extreme positions are on respective opposite sides of the axial position of the reflection surface (31) of the optical element (30).

18. A device according to claim 6, wherein the lighting system includes an auxiliary light source (72) that is annular, having the installation axis (A'1) as an axis thereof, and that is suitable for supplying an annular peripheral incident light beam distinct from the main beam supplied by the main light source (34), the auxiliary beam comprising radial rays contained in a radial plane containing the axis, said radial rays being directed towards the installation axis (A'1), and the auxiliary beam comprising, in a common radial plane, non-parallel radial rays, in that the main and auxiliary light sources (34, 72) are offset along the direction of the installation axis (A'1), and in that the auxiliary source (72) is in a position that is stationary relative to the optical element (30).

19. A device according to claim 18, wherein the main light source (34) is movable between at least two extreme positions along the direction of the installation axis (A'1), both of which are on the same side of the axial position of the reflection surface (31), and in that the auxiliary light source (72) is arranged on the other side of the axial position of the reflection surface (31).

20. A device according to claim 6, wherein the reflection surface (31) is a surface of revolution about the installation axis (A'1) and faces towards the installation axis (A'1), and in that the reflection surface (31) flares along the direction of the installation axis (A'1) and presents a large diameter and a small diameter, both of which are greater than the maximum diameter of the portion of interest (16) of the side wall of the container, the large diameter being arranged below the small diameter.

21. A device according to claim 6, wherein the reflection surface (31) is a frustoconical surface facing towards the installation axis (A'1).

22. A device according to claim 6, wherein the sensor (24) is arranged below the reflection surface (31).

23. A device according to claim 6, wherein the optical system (28) includes an optical objective system (26) associated with the sensor.

24. A device according to claim 6, wherein the container (14) is to be received in the installation zone in such a manner that the theoretical central axis (A1) thereof substantially coincides with the installation axis (A'1).

25. A device according to claim 6, further comprising a base (20), and in that the photoelectric sensor (24) and the optical element (30) are fastened relative to each other and movable relative to the base (40).

26. An inspection line for inspecting containers (14) each presenting portions in relief (12) carried by a bottom portion of an outer side wall (18), the inspection line being of the type in which the containers are moved along a conveyor line by a conveyor that transports the containers (14) in a horizontal travel direction perpendicular to a theoretical central axis (A1) of each container (14), such that the containers present the bottom portions of their outer side walls (18) facing downwards, the inspection line comprising a device (10) for optically reading portions in relief (12) carried by a portion of interest (16) of an outer side wall (18) of a container (14), the device comprising a container installation zone having an installation axis, and further comprising:

a two-dimensional photoelectric sensor (24);

an optical system (28) interposed between the container installation zone and the sensor (24) in order to form on the sensor (24) an image of the portion of interest (16) of the outer side wall (8) of a container (14) placed in the installation zone, the optical system (28) including at least one optical element (30) having a reflection surface of revolution (31) around the installation axis (A'1) and presenting a minimum diameter greater than a maximum diameter of the portion of interest (16) of the outer side wall (18) of a container susceptible of being received in the installation zone;

an optical axis defined by the optical system (28) and extending in the installation zone in order to define the installation axis (A'1); and a lighting system including at least a main light source (34) that is peripheral and has the installation axis (A'1) as an axis thereof, and that is suitable for supplying a peripheral incident light beam in the installation zone, the beam comprising radial rays contained in a radial plane containing the installation axis (A'1), said radial rays being directed towards the installation axis (A'1), and the beam comprising non-parallel radial rays in a common radial plane;

wherein the lighting system (34), the sensor (24), and the optical system (28) are arranged below the installation zone; and further wherein the main light source (34) supplying the peripheral incident light beam is movable in translation along the direction of the installation axis (A'1) relative to the optical element (30), the device arranged on the line with the installation axis (A'1) in a vertical position, such that the incident light beam is upwardly oriented towards the installation zone that is situated between the device and a transport member of the conveyor.

27. An inspection line according to claim 26, wherein the conveyor brings the containers (14) in such a manner that theoretical central axes (A1) thereof coincide with the installation axis (A'1), and when the theoretical central axes (A1) the installation axis (A'1) are in coincidence, an image is acquired using the device (10), without the device (10) making contact with the container (14).

* * * * *